United States Patent
Dietz et al.

(10) Patent No.: US 6,800,156 B2
(45) Date of Patent: Oct. 5, 2004

(54) SURFACE PREPARATION INDICATORS

(75) Inventors: Timothy M. Dietz, Mendota Heights, MN (US); Gerald F. Fleischhacker, White Bear Lake, MN (US); Larry S. Hebert, Hudson, WI (US); Thomas J. Packard, Somerset, WI (US); Mark D. Weigel, Hugo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/211,361

(22) Filed: Aug. 2, 2002

(65) Prior Publication Data

US 2004/0020592 A1 Feb. 5, 2004

(51) Int. Cl.⁷ ................................................ B32B 31/00
(52) U.S. Cl. ........................ 156/64; 158/344; 73/150 A
(58) Field of Search .......................... 156/64, 344, 584, 156/598; 73/150 A; 428/317.7, 355 R

(56) References Cited

U.S. PATENT DOCUMENTS

| | | |
|---|---|---|
| 4,188,824 A | 2/1980 | McCarthy |
| 5,516,581 A | 5/1996 | Kreckel et al. |
| 5,649,447 A | 7/1997 | Van Avery |

*Primary Examiner*—Richard Crispino
*Assistant Examiner*—George R. Koch, III
(74) *Attorney, Agent, or Firm*—Scott A. Bardell

(57) ABSTRACT

The present invention relates to indicators of surface preparation and methods of making such indicators.

13 Claims, 2 Drawing Sheets

SURFACE PREPARATION INDICATORS

FIELD OF THE INVENTION

The present invention relates to indicators of surface preparation and methods of making such indicators.

BACKGROUND OF THE INVENTION

Typically, the application of coatings to a surface of a substrate requires proper surface preparation to provide adequate bonding between the coating and the surface. Examples of such coatings include paints, adhesives, primers, and the like. Surface preparation is performed to remove surface contaminates such as dust, fluids, oils, dirt, and the like, to obtain a desired surface cleanliness and/or to improve adhesion of the coating to the surface. A properly prepared surface may also be contaminated prior to the application of the coating. It would be desirable to provide an easy, inexpensive way of testing a surface just prior to the application of a coating or adherent to determine if additional surface preparation is required to provide an adequate bond between the surface and the coating.

SUMMARY OF THE INVENTION

In one embodiment, the invention provides a method of directly indicating the propensity of an adherent or coating to bond to a surface of a substrate. The steps of the method comprise applying a surface preparation indicator to the surface of the substrate wherein the substrate has a desired or target adhesion force to a coating. The surface preparation indicator comprises a polymeric backing material having a yield point and an adhesive on the backing. The target adhesive force and the force required to reach the yield point of the indicator are substantially the same.

In another embodiment, the invention provides a method of designing a surface preparation indicator for a particular substrate and adherent or coating combination. This method comprises the steps of providing a target adhesion force for the adherent to an acceptable surface of a substrate; selecting an adhesive that provides an adhesion to the acceptable surface that is equal to or greater than the target adhesion force and that provides an adhesion that is less than the target adhesion force when the surface of the substrate is not acceptable; selecting a backing material having a yield point and that bonds to the selected adhesive such that the backing material and the adhesive will not separate when subject to applied force that is lower than that of the target adhesion force; configuring said backing material such that the applied force required to reach the yield point is substantially the same as the target adhesion force; and bonding the selected adhesive to the backing material.

A "yield point" is the point at which, after an initial applied stress, a further applied stress causes appreciable elongation or yield in a material without the application of comparable additional stress. In other words, a "yield point" is the point at which, after an initial applied stress, appreciable elongation or yield in a material is obtained without the application of comparable additional stress. A material stressed beyond its yield point will have permanent deformation.

"Adhesive" means any substance that is capable of bonding to other materials by surface attachment.

DETAILED DESCRIPTION OF THE PREFERRED EMBODIMENTS

In general, the method of the invention provides a quick, easy, and reliable means to indicate whether a surface is properly prepared to receive a coating, for example, a primer, paint, or an adhesive of choice. Simply, a specifically designed permanently deformable indicator, for example, in the form of a strip, is bonded to the surface of the substrate to be tested. A method for designing such an indicator strip is described below. The bonded indicator strip is pulled in an effort to remove it. If the specifically designed indicator strip yields or permanently deforms while being pulled away from the substrate, the surface would be considered properly prepared. However, if the specifically prepared test strip is pulled away from the surface before the indicator strip permanently deforms, the surface would be considered not properly prepared and further preparation, for example, cleaning, would be required.

Figure 1:
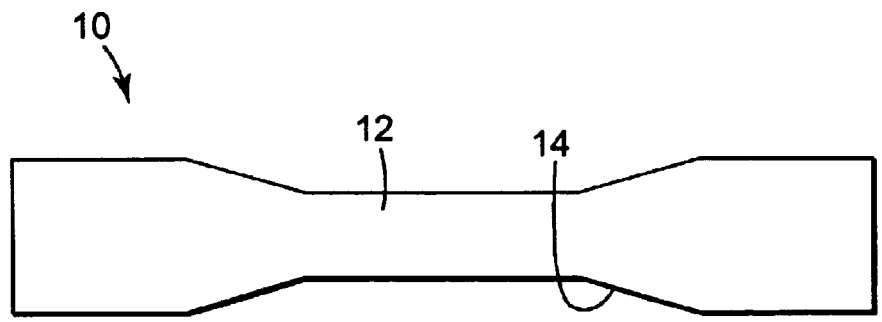
FIG. 1 is a plan view of one embodiment of the invention.

FIG. 1 shows one embodiment of a specifically prepared indicator that permanently deforms at an applied force. The indicator 10 comprises a backing 12 made from a material that has a yield point and an adhesive 14 on the backing. The indicator is generally "dogbone" shaped.

Figure 2:
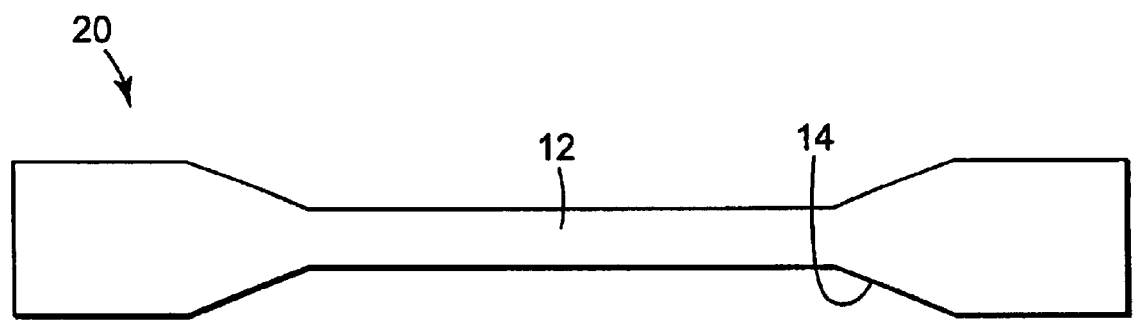
FIG. 2 is plan view of an embodiment of the invention after yielding.

FIG. 2 shows a depiction of an indicator 20 after it has been permanently deformed from an applied stress.

Figure 3:
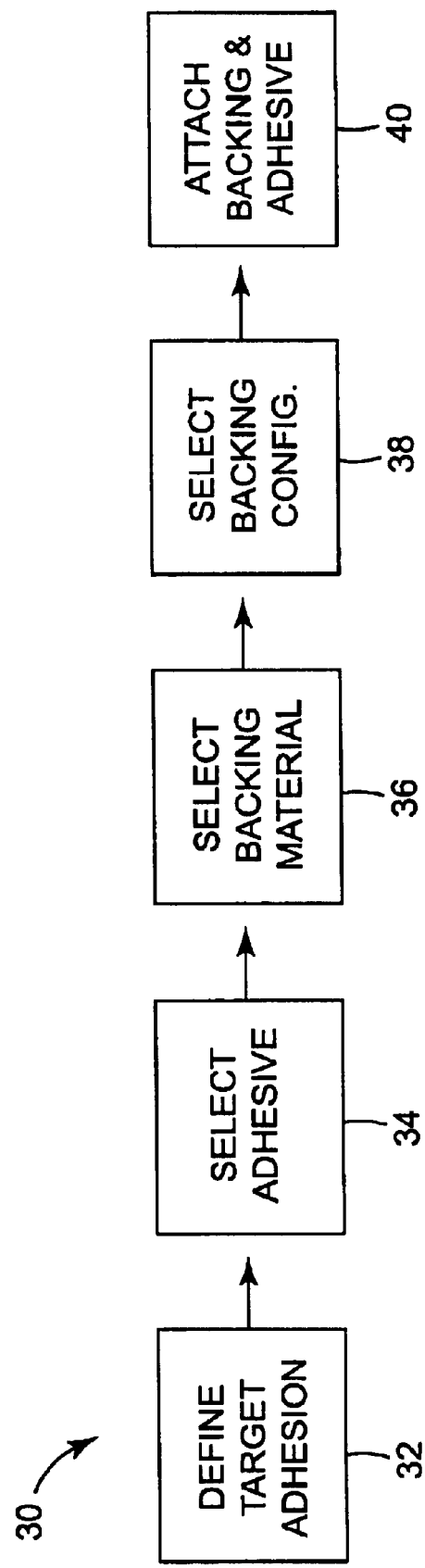
FIG. 3 is a process flow diagram for making an indicator of the invention having the desired characteristics.

FIG. 3 shows a flow diagram 30 of a process to design a specifically designed adhesion or surface preparation indicator. Generally, the process comprises the steps of: defining the target adhesion force 32 for a particular surface; selecting a suitable adhesive 34; selecting a material that permanently deforms under an applied stress 36; selecting a backing configuration that permanently deforms at the applied target adhesion force but does not permanently deform below the target adhesion force 38; and attaching the adhesive to the selected backing 40 so to form an indicator.

The target adhesion force is typically set by a specification or requirement set by a party such as a customer. For example, an adhesive film specification may be an adhesion or peel strength of 0.11 pounds force per inch width for a particular substrate. The target adhesion force may also be determined by measurement. For example, a coating may be applied to a substrate and then the force required to remove a specified area of the coating could be measured using a simple scale or a sophisticated machine such as an INSTRON brand instrument.

A "suitable" adhesive is an adhesive that meets or exceeds the target adhesion force after attachment to the substrate when the surface of the substrate is properly prepared (acceptable), for example, clean, and/or an adhesive that does not meet the target adhesion force when the surface of the substrate is not properly prepared (not acceptable), for example, dirty or contaminated. Of course, the determination of a properly prepared surface and an un-properly prepared surface is typically determined by trial and error before an adhesive is selected. The suitable adhesive for the indicator may be the same or different than the adhesive or coating that will be used to bond to or coat the substrate. A suitable adhesive may also be identified through simple testing of the adhesion force of different adhesives on "clean" surfaces and on "dirty" surfaces as described above for determining the target adhesion force.

A suitable adhesive is also an adhesive that forms a bond with the backing material, discussed below, such that the bond between the adhesive and the backing material does not fail, that is, separate, below the target adhesion force when pulling on the indicator. The bond strength between adhesives and proposed backing materials can easily be determined by bonding samples together and then measuring the adhesion force between them. If the adhesion force is below that of the target adhesion force, another adhesive and/or film and adhesive combination may be tested until the desired target adhesion force is met.

The adhesive selected may be pressure sensitive, hot melt, curable, thermoset, contact, thermoplastic, crosslinking, or any combination of these. Specific examples include acrylics, epoxies, urethanes, amides, natural or synthetic rubbers, olefins, cyanoacrylates, silicones, and the like and combinations thereof.

The step of selecting a material that permanently deforms or yields under an applied stress may be performed simply by selecting materials, for example, polymer films, and applying a stress to them and noting whether they have a yield point, that is, the material permanently deforms after applying stress or stretching it. The yield point of the material should bear some relationship to the target adhesion point. In other words, one probably would not select a material having a yield point of 10 grams force where the target adhesion force is, for example, 0.01 grams per specified width. Examples of materials that have a yield point are polyethylene, polypropylene, plasticized polyvinyl chloride, and terpolymers of vinylidine fluoride, hexafluoropropylene, and tetrafluoroethylene sold under the designation "THV 500", available from 3M Company, St. Paul, Minn., and the like and combinations thereof.

Once a material having a yield point is selected, a backing configuration that permanently deforms at the applied target adhesion force but does not permanently deform at applied forces below the target adhesion force is selected. One means of selecting such a configuration is to cut a piece of the backing material having a certain cross-sectional area (thickness and width) and then measuring the force required to permanently deform that sample. Then, the shape and/or thickness of the backing material can be modified as (or if) required to achieve the yield point that matches the target adhesive force. For example, increasing the cross-sectional area of the sample will likely increase the force required for the material to reach its yield point, while decreasing the cross-sectional area will likely decrease the amount of force needed to reach the yield point. The cross-sectional area may be changed by increasing or decreasing the width and/or thickness of the sample. Thus, one could construct correlation charts for each particular backing material that may be of interest. Backing thickness generally ranges from about 0.5 to about 50 mil and may be any whole or fractional thickness between 0.5 and 50 mil.

The force required to reach the yield point for a given backing material should be substantially the same as the target adhesion force and preferably, not below the target adhesion force (assuming that the adhesive does not alter the yield point of the backing). "Substantially the same" means, for a particular backing material, within the experimental error as determined by a generally accepted materials testing protocol in the relevant art. The force required to reach the yield point of the backing material may be above the target adhesion force. However, the higher the yield point force is above the target adhesion force, the more likely it is to obtain false indications of un-properly prepared surfaces.

Typical yield forces range from about 0.1 to about 20 pounds force and may be any whole or fractional value in between 0.1 and 20 pounds force.

Once a backing configuration is selected, the suitable adhesive is bonded to the backing. This may be done by any of the known bonding methods, for example, solvent coating, hot melt coating, lamination, extrusion, etc., and may include treating the surface of the backing with a primer, by corona exposure, electron beam, and the like. The adhesive may be in the form of a liquid, powder, solid, or film. The adhesive may be coated over the full or a partial area of the appropriate backing surface.

The substrates may be comprised of any material to which an adhesive (as defined) will form a bond with. Examples include, metals, glass, plastics, ceramics, masonry, plaster, paper, wood, fiber reinforced plastics, and the like and combinations thereof.

EXAMPLES

Example 1

The indicator used in Example 2 was designed as follows:

The target adhesion force was defined as 40 ounces per inch width at ambient temperature 32. An acrylic pressure-sensitive adhesive which adhered to a cleaned aluminum surface at a force of greater than 40 ounces per inch width and at a force of less than the target force when the surface was contaminated was selected by testing the adhesion performance of a plurality of acrylic adhesive compositions known to provide adhesion to aluminum surfaces 34. A fluoropolymer thermoplastic film was selected as the permanently deformable backing material based on knowledge of the film's physical characteristics, for example, having a yield point, and being bondable to an acrylic adhesive 36. The film configuration was selected by testing the yield points of film strips having a uniform width of 1 inch; a partial width of ¾ inch, a partial width of ¼ inch, a partial width of ½ inch, and a partial width of ⅝ inch. Partial width refers to the narrow portion of the dogbone shape. The selected adhesive was then coated onto the selected backing and dried, and the indicator was configured to the final form 40.

Example 2

Surface preparation indicators were prepared by coating the primed surface of a yielding polymer film (3951 Surface Protection film, 3.5 mil, available from 3M Company) with a layer of acrylic pressure-sensitive adhesive and a release liner was applied to the exposed surface of the pressure-sensitive adhesive. The polymer film/adhesive/release liner construct was then cut into specimens using a die. The resulting specimens were dogbone shaped, having dimensions of 1 inch×7 inches, with a 0.5 inch wide by 1 inch long neck beginning 1 inch from one end of the test strip.

The adhesive was prepared by mixing 70 parts by weight isooctyl acrylate, 56 parts by weight ethyl acrylate, 14 parts by weight acrylic acid, 260 grams ethyl acetate, and 0.42 grams benzoyl peroxide in a container with nitrogen purging. The container was sealed and rotated in a water bath at 59° C. for 24 hours. The resulting solution was diluted to 21% solids with heptane. Next, 2.1 parts of a 5% (w/w) solution of N,N'-bis-1,2-propyleneisophthalamide in toluene was added prior to coating onto the yielding polymer film. The adhesive was dried in a convection oven set at 200° F. for 10 minutes.

A specimen was applied by peeling back the release liner from the adhesive and then attaching the strip adhesive down to a 2024-T3 bare aluminum surface that had been cleaned with isopropanol. The specimen was removed by hand by pulling on the end of the specimen nearest the dogbone at an angle of about 180 degrees at a rate of about 12 inch/minute. The specimen yielded, thus indicating correct surface preparation.

Example 3

The procedure of Example 2 was repeated except the surface of the aluminum panel was contaminated with a detergent after it had been properly cleaned. The specimen was removed from the substrate without yielding.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of directly indicating the propensity of an adherent to bond to a surface of a substrate comprising the steps of:
    applying a surface preparation indicator to the surface of the substrate wherein the substrate has a target adhesion force, said surface preparation indicator comprising a polymeric backing material having a yield point and having an adhesive thereon and having a thickness, width, and length, wherein the target adhesive force and the force required to reach the yield point are substantially the same; and
    applying force to said indicator until the indicator either reaches the yield point or is removed from the substrate.

2. The method of claim 1, wherein the backing material comprises polyethylene, polypropylene, plasticized polyvinyl chloride, a terpolymer of vinylidine fluoride, hexafluoropropylene, and tetrafluoroethylene, and combinations thereof.

3. The method of claim 1, wherein the adhesive comprises acrylics, epoxies, urethanes, amides, natural or synthetic rubbers, olefins, cyanoacrylates, silicones, and combinations thereof.

4. The method of claim 1, wherein the surface preparation indicator consists essentially of a polymeric backing material having a yield point and having an adhesive on the backing film.

5. The method of claim 1, wherein the force required to reach the yield point of the backing material is less than 50 pounds force.

6. The method of claim 1, wherein the surface of the substrate comprises metal.

7. The method of claim 1, wherein the surface of the substrate is selected from the group consisting of metals, glass, plastics, ceramics, masonry, plaster, paper, wood, fiber reinforced plastics, and combinations thereof.

8. The method of claim 1, wherein the force required to reach the yield point of the backing material is greater than 0.1 pounds force.

9. The method of claim 1, wherein the surface preparation indicator has a non-uniform width along its length.

10. The method of claim 1, wherein the step of applying the indicator to a surface of the substrate indicates application of pressure.

11. The method of claim 1, wherein the adhesive is a pressure-sensitive adhesive at the application temperature.

12. The method of claim 1, wherein the adhesive is a pressure-sensitive adhesive at ambient temperature.

13. The method of claim 1, wherein the step of applying force comprises a 180 degree peel procedure.

* * * * *